United States Patent [19]

McEntire

[11] 4,374,259

[45] Feb. 15, 1983

[54] PROCESS FOR CONVERTING SUBSTITUTED ETHYLENE CARBONATES INTO SUBSTITUTED ETHYLENE OXIDES USING TIN CATALYSTS

[75] Inventor: Edward E. McEntire, Austin, Tex.

[73] Assignee: Texaco Development Corporation, White Plains, N.Y.

[21] Appl. No.: 95,031

[22] Filed: Nov. 16, 1979

Related U.S. Application Data

[63] Continuation-in-part of Ser. No. 920,906, Jun. 29, 1978, abandoned.

[51] Int. Cl.$^3$ ........................................... C07D 317/36
[52] U.S. Cl. .................................................. 549/518
[58] Field of Search ............................... 314/920, 906; 260/348.16, 348.16; 549/518

[56] References Cited

U.S. PATENT DOCUMENTS 3,806,467  4/1974  Watanabe et al. ............. 260/348.31
4,069,234  1/1978  Wu .................................. 260/348.16

FOREIGN PATENT DOCUMENTS 1276637  7/1972  United Kingdom ........... 260/348.29

*Primary Examiner*—Norma S. Milestone
*Attorney, Agent, or Firm*—Robert A. Kulason; Kenneth R. Priem; David L. Mossman

[57] ABSTRACT

Alkyl substituted ethylene carbonates are converted to substituted ethylene oxide by heating the carbonates in the presence of a catalytic amount of a compound containing at least one carbon-tin bond. The alkyl substituted ethylene carbonates have the general formula

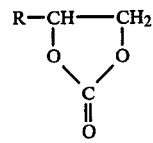

where R is alkyl, aryl, substituted alkyl, substituted aryl, alkaryl or aralkyl.

25 Claims, No Drawings

PROCESS FOR CONVERTING SUBSTITUTED ETHYLENE CARBONATES INTO SUBSTITUTED ETHYLENE OXIDES USING TIN CATALYSTS

This application is a continuation-in-part of application Ser. No. 920,906 filed June 29, 1978, abandoned.

BACKGROUND OF THE INVENTION

1. Field of the Invention

This invention relates to the preparation of substituted ethylene epoxides.

2. Discussion of Prior Art

Substituted ethylene epoxides such as propylene oxide and butylene oxide, etc. are well known in the art as monomers used in the preparations of resins of various types ranging from epoxy adhesive application to elastomeric solvent resistant polymers for use in making tubing, shoe soles and the like. These epoxides are also useful in the preparation of polyols for use in polyurethane foams. These substituted ethylene epoxides can be prepared by the direct oxidation of an olefin or by treatment of the corresponding halohydrin with lime. These processes have yet to be perfected and the direct oxidation routes are especially difficult due to the formation of a variety of by-products which render the processes uneconomical.

It is disclosed in U.S. Pat. No. 4,069,234 that substituted ethylene carbonates may be converted to substituted ethylene epoxides using various catalysts including tin(II) carboxylates. Stannous acetate is specifically mentioned.

In accordance with the present invention, it has been discovered that substituted ethylene epoxides may be prepared from substituted ethylene carbonates by catalytic conversion using catalysts containing at least one carbon-tin bond wherein the tin is tin(IV). These compounds are generally known as organo-metallic compounds specifically organo-tin compounds. It is recognized in the art that the tin compounds containing carbon-tins bonds are a separate and distinct class of compounds from the tin(II) compounds of the U.S. Pat. No. 4,069,234 mentioned above. For example, in the publication, Organo Metallic Compounds, volume 2, Springer-Verlag, New York, Inc. 1967 at the preface at page V it is stated:

"The aim of this compilation has been to provide a comprehensive, non-critical source of information concerning organic-metallic compounds. The scope is limited to the compounds containing at least one carbon-metal bond."

Thus, the present invention discloses that substituted ethylene carbonates may be converted into substituted ethylene epoxides using new catalysts heretofore not disclosed by the prior art.

SUMMARY OF THE INVENTION

The invention is a process of convering substituted ethylene carbonates into substituted ethylene oxides using organo-tin(IV) catalysts. The organo-tin(IV) catalysts may be further classified as
 (a) alkyl tin oxides
 (b) alkyl tin acids
 (c) polyalkyl tin compounds
 (d) polyalkyl tin carboxylates
 (e) dialkyl in tin alkoxides.

The conversion may take place in the liquid phase at about 150°–250° C. in a batch or continuous reaction. An inert solvent is optional.

DESCRIPTION OF THE PREFERRED EMBODIMENTS

The present invention is a method for converting substituted ethylene carbonates of the formula

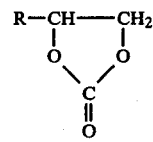

wherein R is alkyl, aryl, substituted alkyl, substituted aryl, alkaryl or aralkyl and preferably wherein R is an alkyl group of from 1 to 20 carbon atoms and more preferably from 1 to 7 carbon atoms and still more preferably wherein R is one carbon atom and the substituted ethylene carbonate is propylene carbonate into the corresponding substituted ethylene oxide in the presence of a catalytic amount of an organo-tin(IV) catalyst. The catalyst useful in my invention may be further defined in five categories:

(a) alkyl tin oxides
  $R_2SnO$ wherein R is an alkyl from 1 to about 20 carbon atoms
  $(R_3Sn)_2O$ wherein R is an alkyl from 1 to about 20 carbon atoms
(b) alkyl tin acids
  $RSnO_2H$ wherein R is an alkyl from 1 to about 20 carbon atoms
(c) polyalkyl tin compounds
  $SnR_4$ wherein R is an alkyl from 1 to about 20 carbon atoms
  $R_6Sn_2$ wherein R is an alkyl from 1 to about 20 carbon atoms and the R groups may be the same or different
(d) polyalkyl tin carboxylates

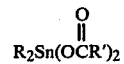

wherein R and R' are alkyl groups from 1 to about 20 carbon atoms and R and R' may be the same or different

wherein R and R' are alkyl groups from 1 to about 20 carbon atoms and R and R' may be the same or different
(e) dialkyl tin alkoxides
  $R_2Sn(OR'')(OR''')$ wherein R, R' and R'' are alkyl groups from 1 to about 20 carbon atoms and R, R' and R'' may be the same or different.

The process of my invention should be performed in the liquid phase at a temperature ranging from about 150° to 300° C. preferably to about 250° C. A batch or continuous reaction may be used. An inert solvent is optional. The pressure may range from about 0.05 to about 10 atmospheres.

The amount of catalyst may vary depending on the selection of the above variables as well as which substituted ethylene carbonate is chosen. In the experiments which follow, the amount of catalyst based on substituted ethylene carbonate ranged from about 2 to 5 weight percent. Amounts ranging from about 0.01 to 100 weight percent of the substituted ethylene carbonate are recommended.

EXPERIMENTAL

An attempt to convert ethylene carbonate itself to ethylene oxide using the tin catalysts above resulted in very little ethylene oxide produced. The selectivity in these reactions is primarily to p-dioxane and nonvolatile materials. Conversion of substituted ethylene carbonate principally propylene carbonate resulted in very high yields of propylene oxide as shown by the Examples to follow. The examples were conducted by heating 200 g of propylene carbonate with the desired amount of the tin catalyst chosen. Overhead was collected with a dry ice cooled condensor. Analyses were conducted by gas-liquid chromatography. Calculations were made as follows:

% Conversion =

$$\frac{\text{wt. P.C. charged} - (\text{wt. Bottoms} - \text{wt. Catalyst})}{\text{wt. P.C. charged}} \times 100$$

$$\% \text{ Yield} = \frac{\text{wt. Overhead} \times \% \text{ Oxide in Overhead}}{\text{Theoretical wt. Oxide from total P.C. charged}}$$

$$\% \text{ Selectivity} = \frac{\% \text{ Yield}}{\% \text{ Conversion}} \times 100$$

from propylene carbonate, their selectivity to propylene oxide is much poorer than that of the organo-tin catalysts of preference. The results of these less efficient inorganic tetravalent tin experiments are presented in Table II.

A further experiment described in Table II uses an organic divalent tin catalyst, stannous acetate, in an attempt to make propylene oxide. While the selectivity to propylene oxide was fairly good, the conversion of propylene carbonate was very low making stannous acetate an inefficient catalyst for propylene oxide production.

It may be seen that the organo-tetravalent tin catalysts of my invention give surprisingly good results in making substituted ethylene oxides from substituted ethylene carbonates. This novel discovery is far beyond what could be expected from the teaching of U.S. Pat. No. 4,069,234 with respect to tin compounds as catalysts.

TABLE II

| Experiment Number | Catalyst (g) | Wt. Overhead (g) | Wt. Bottoms (g) | Heating Time (hr) | Temp. Range °C. | Conv. P.C. (%) | Selectivity (%) | % P.O. in Overhead |
|---|---|---|---|---|---|---|---|---|
| 10 | Strontium Stannate (5) | 19 | 150 | 5 | 228–234 | 27.5 | 56.0 | 92.1 |
| 11 | Potassium Stannate (5) (K$_2$SnO$_3$) | 46 | 79 | 5 | 182–202 | 63.0 | 40.5 | 63.0 |
| 12 | Stannous Acetate (4.79) (Sn(OAc)$_2$) | 25 | — | 4.2* | 200–223 | 17.8 | 90.0 | 91.0 |

*Reaction was essentially complete after 40 min. of heating; catalyst would deactivate with propylene carbonate as a substrate.

I claim:

1. A process for the preparation of a substituted ethylene epoxide of the formula

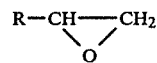

wherein R is alkyl, aryl, substituted alkyl or substituted aryl which comprises heating the corresponding substituted ethylene carbonate having the formula

TABLE I

| Experiment Number | Catalyst (g) | Wt. Overhead (g) | Wt. Bottoms (g) | Heating Time (hr) | Temp. Range °C. | Conv. P.C. (%) | Selectivity (%) | % P.O. in Overhead |
|---|---|---|---|---|---|---|---|---|
| 1 | Bu$_2$SnO (5) | 58 | 94 | 6.0 | 232–236 | 50.5 | 97.4 | 96.4 |
| 2 | Bu$_6$Sn$_2$ (5) | 42 | 132 | 6.0 | 235–238 | 36.5 | 94.1 | 93.0 |
| 3 | Bu$_2$Sn(Laur)$_2$(10) | 8 | 180 | 4.3 | 235–236 | 15.0 | 44.2 | 94.2 |
| 4 | Bu$_4$Sn (5) | 23 | 164 | 5.0 | 230 | 20.5 | 95.0 | 96.3 |
| 5 | Bu$_2$Sn(O—CHCH$_3$)$_2$ (5) | 38 | 131 | 5.0 | 224–236 | 37.0 | 88.5 | 98.0 |
| 6 | Bu$_3$SnOAc(7) | 15 | 170 | 5.0 | 224–231 | 18.5 | 64.6 | 90.6 |
| 7 | (Bu$_3$Sn)$_2$O(6) | 22 | 164 | 5.0 | 232–238 | 21.0 | 83.8 | 90.9 |
| 8 | (Octyl)$_2$SnO(7.25) | 101 | 20 | 4.3 | 180–225 | 93.6 | 90.8 | 95.7 |
| 9 | BuSnO$_2$H(4.2) | 95 | 48 | 11.0 | 200–210 | 79.1 | 92.7 | 92.1 |

Bu = n-butyl
P.C. = Propylene Carbonate
P.O. = Propylene Oxide
Laur. = laurate

Two experiments were performed using inorganic tetravalent tin catalysts under conditions similar to the organo-tetravalent tin catalyst experiments in Table I. While the inorganic catalysts will make propylene oxide

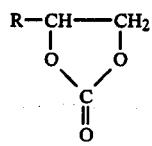

wherein R is defined as above in the presence of a catalytic amount of an organo-tin catalyst wherein the tin is tin(IV).

2. The process of claim 1 wherein the substituted ethylene carbonate is heated in the presence of said catalyst at a temperature in the range from 150° to 300° C. and a pressure ranging from about 0.05 to 10 atmospheres.

3. The process of claim 1 wherein said catalyst is present in an amount ranging from about 0.01 to 100 weight percent in the substituted ethylene carbonate.

4. The process of claim 1 wherein R is alkyl.

5. The process of claim 1 wherein said substituted ethylene carbonate is propylene carbonate.

6. A process for the preparation of a substituted ethylene epoxide of the formula

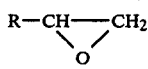

wherein R is alkyl which comprises heating the corresponding substituted ethylene carbonate having the formula

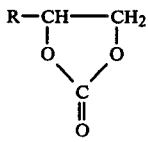

wherein R is defined as above in the presence of a catalytic amount of an organo-tin oxide wherein the tin is tin(IV).

7. The process of claim 6 wherein the substituted ethylene carbonate is heated in the presence of said catalyst at a temperature in the range of from 150° to 300° C. and a pressure ranging from about 0.05 to 10 atmospheres.

8. The process of claim 6 wherein said catalyst is present in an amount ranging from about 0.01 to 100 weight percent of the substituted ethylene carbonate.

9. The process of claim 6 wherein said substituted ethylene carbonate is propylene carbonate.

10. A process for the preparation of a substituted ethylene epoxide of the formula

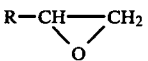

wherein R is alkyl which comprises heating the corresponding substituted ethylene carbonate having the formula

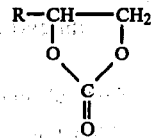

wherein R is defined as above in the presence of a catalytic amount of alkyl tin acids wherein the tin is tin(IV).

11. The process of claim 10 wherein the substituted ethylene carbonate is heated in the presence of said catalyst at a temperature in the range of from 150° to 300° C. and a pressure ranging from about 0.05 to 10 atmospheres.

12. The process of claim 10 wherein said catalyst is present in an amount ranging from about 0.01 to 100 weight percent of the substituted ethylene carbonate.

13. The process of claim 10 wherein said substituted ethylene carbonate is propylene carbonate.

14. The process for the preparation of a substituted ethylene epoxide of the formula

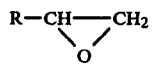

wherein R is alkyl which comprises heating the corresponding substituted ethylene carbonate having the formula

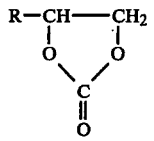

wherein R is defined as above in the presence of a catalytic amount of a polyalkyl tin compound wherein the tin is tin(IV).

15. The process of claim 14 wherein the substituted ethylene carbonate is heated in the presence of said catalyst at a temperature in the range of from 150° to 300° C. and a pressure ranging from about 0.05 to 10 atmospheres.

16. The process of claim 14 wherein said catalyst is present in an amount ranging from about 0.01 to 100 weight percent of the substituted ethylene carbonate.

17. The process of claim 14 wherein said substituted ethylene carbonate is propylene carbonate.

18. The process for the preparation of a substituted ethylene epoxide of the formula

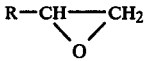

wherein R is alkyl which comprises heating the corresponding substituted ethylene carbonate having the formula

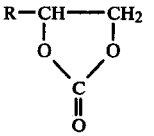

wherein R is defined as above in the presence of a catalytic amount of polyalkyl tin carboxylate wherein the tin is tin(IV).

19. The process of claim 18 wherein the substituted ethylene carbonate is heated in the presence of said catalyst at a temperature in the range of from 150° to 300° C. and a pressure ranging from about 0.05 to 10 atmospheres.

20. The process of claim 18 wherein said catalyst is present in an amount ranging from about 0.01 to 100 weight percent of the substituted ethylene carbonate.

21. The process of claim 18 wherein said substituted ethylene carbonate is propylene carbonate.

22. A process for the preparation of a substituted ethylene epoxide of the formula

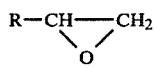

wherein R is alkyl which comprises heating the corresponding substituted ethylene carbonate having the formula

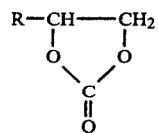

wherein R is defined as above in the presence of a catalytic amount of dialkyl tin alkoxide wherein the tin is tin(IV).

23. The process of claim 22 wherein the substituted ethylene carbonate is heated in the presence of said catalyst at a temperature in the range of from 150° to 300° C. and a pressure ranging from about 0.05 to 10 atmospheres.

24. The process of claim 22 wherein said catalyst is present in an amount ranging from about 0.01 to 100 weight percent of the substituted ethylene carbonate.

25. The process of claim 22 wherein said substituted ethylene carbonate is propylene carbonate.

* * * * *